United States Patent [19]

Yamaguchi et al.

[11] 4,450,725

[45] May 29, 1984

[54] ELECTROMAGNETIC-ACOUSTIC MEASURING APPARATUS

[75] Inventors: Hisao Yamaguchi; Kazuo Fujisawa, both of Amagasaki; Takashi Kadowaki, Hitachi; Susumu Itoh, Hitachi; Soji Sasaki, Hitachi; Ichiya Sato, Hitachi, all of Japan

[73] Assignees: Hitachi, Ltd.; Sumitomo Metal Industries, Ltd., both of Tokyo, Japan

[21] Appl. No.: 386,445

[22] Filed: Jun. 9, 1982

[30] Foreign Application Priority Data

Jun. 10, 1981 [JP] Japan .................................. 56-88188
Jun. 10, 1981 [JP] Japan .................................. 56-88189
Apr. 14, 1982 [JP] Japan .................................. 57-61126

[51] Int. Cl.³ .................... G01N 29/00; G01N 29/04
[52] U.S. Cl. .................................................. 73/643
[58] Field of Search .................. 73/643; 335/281, 258

[56] References Cited

U.S. PATENT DOCUMENTS

| 3,697,867 | 10/1972 | Kleesattel | 73/643 |
|---|---|---|---|
| 4,034,841 | 1/1977 | Ohyama | 335/258 |
| 4,184,374 | 1/1980 | Thompson et al. | 73/643 |
| 4,309,905 | 1/1982 | Maizenberg | 73/643 |
| 4,348,903 | 9/1982 | Sato et al. | 73/643 |

FOREIGN PATENT DOCUMENTS

| 2008756 | 6/1979 | United Kingdom | 73/643 |
|---|---|---|---|
| 543868 | 5/1977 | U.S.S.R. | 73/643 |

OTHER PUBLICATIONS

"Electromagneto-Acoustic Non-Destructive Testing in the Soviet Union," Butenko et al, *Non-Destructive Testing,* vol. 5, No. 3, Jun. 1972, pp. 154–159.

*Primary Examiner*—Howard A. Birmiel
*Attorney, Agent, or Firm*—Antonelli, Terry & Wands

[57] ABSTRACT

An electromagnetic-acoustic measuring apparatus is disclosed in which an exciting coil is wound around a body to be inspected in order to generate a magnetic field within the body in the direction parallel to a surface of the body, a transmitting coil is used to generate mechanical strain in the surface of the body by utilizing the magnetic field, a receiving coil detects the mechanical strain at the surface of the body after the mechanical strain has been propagated in the body, the exciting coil is enclosed with a separable core, the transmitting and receiving coils are supported by respective head portions of pole pieces fixed to the core, and the transmitting and receiving coils and pole pieces are water-cooled by means of cooling pipes.

15 Claims, 8 Drawing Figures

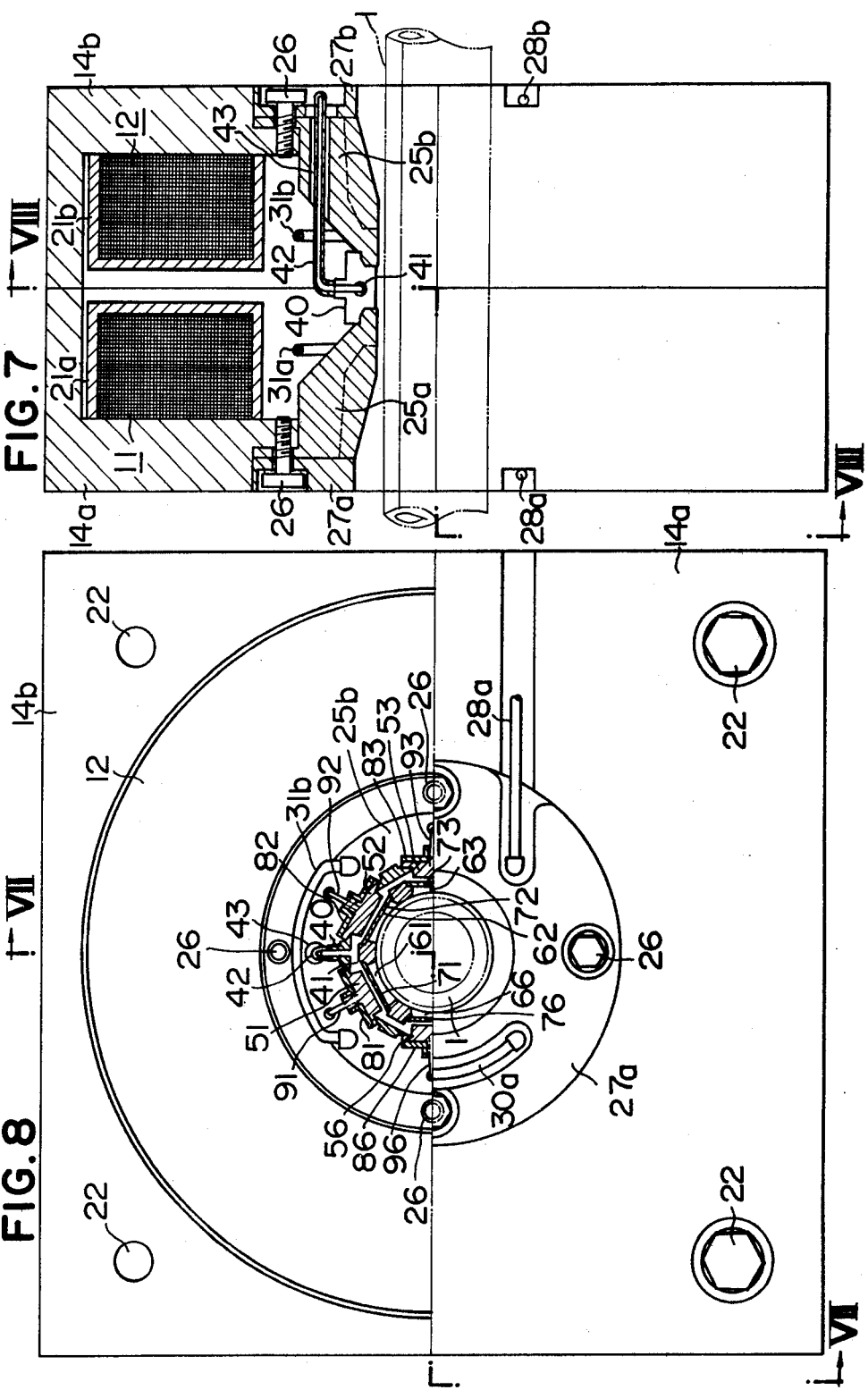

ELECTROMAGNETIC-ACOUSTIC MEASURING APPARATUS

The present invention relates to electromagnetic-acoustic measuring apparatuses.

Ultrasonic inspection methods, which are non-destructive inspection methods, are used in various field of technology. However, such methods have two drawbacks, (1) the surface of a body to be inspected must be smooth and (2) it is impossible to inspect a body at high temperatures. Electromagnetic-acoustic measuring apparatuses which can eliminate these drawbacks have been widely studied and, in some cases, have been put to practical use. Electromagnetic-acoustic measuring methods are described in detail in the article "Electromagneto-acoustic non-destructive testing in the Soviet Union" by Butenko et al, in the journal Nondestructive Testing, Vol. 5, No. 3, June 1972, pages 154 to 159.

According to the principle inherent in the electromagnetic-acoustic method, in order to detect flaws within a body under inspection or to accurately measure the thickness of the body, it is necessary to generate a strong magnetic field across the surface of the body and/or to increase the power of the signal supplied to a transmitting coil. Since the power of the signal supplied to the transmitting coil must be limited for safety reasons, the only recourse is to increase the intensity of the magnetic field. However, in conventional methods, a magnetic field is generated across the surface of the body under inspection with an E-shaped iron core and, therefore, the intensity of the magentic field is limited.

In an electromagnetic-acoustic measuring apparatus, either longitudinal or transverse ultrasonic waves can be used, depending on the purpose of measurement. When a longitudinal wave is used in the inspection of a body at relatively high temperatures, it is necessary to generate a magnetic field parallel to the surface of the body. However, in the case where an E-shaped iron core is used, the body to be inspected acts merely as a yoke and, therefore, it is impossible to generate a magnetic field parallel to the surface of the body.

Accordingly one purpose of the present invention is to provide an electromagnetic-acoustic measuring apparatus which can generate a magnetic field parallel to the surface of a body to be inspected.

In order to attain this objective, the body to be inspected is inserted in the opening of the exciting coil, so that substantially all of the magnetic motive force (expressed in ampere-turns) produced by the exciting coil is applied parallel to that body. As a result, the strength of the magnetic field component parallel to the surface of the body is increased and, therefore, electromagnetic-acoustic measurements can be carried out with a longitudinal wave.

The above features and advantages of the present invertion will become more apparent from the following description and the accompanying drawings.

BRIEF DESCRIPTION OF THE DRAWINGS

FIG. 7 is a side view of the embodiment shown in FIG. 6, in partial cross section, viewed in the direction indicated by the arrows VII; and FIG. 8 is a front view of the embodiment shown in FIG. 6, in partial cross section, viewed in the direction indicated by the arrows VIII. Both views show the detailed structure of the embodiment.

Various embodiments of the present invention will be explained in detail below, reference to the drawings.

Figure 1:
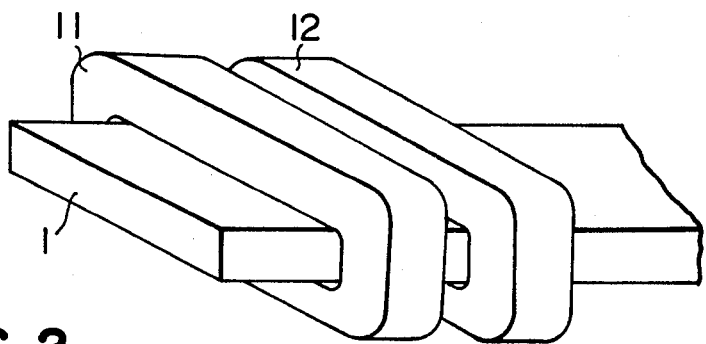
FIG. 1 is a perspective view of the fundamental embodiment of the present invention.
Figure 2:
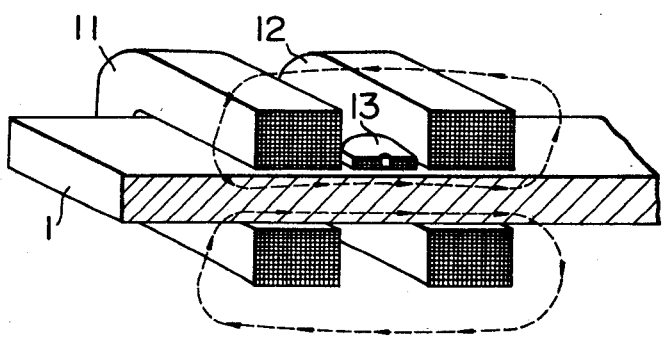
FIG. 2 is a perspective view of the invention in cross section, showing the positions of the exciting coils shown in FIG. 1 in relation to a transmitting/receiving coil.

FIGS. 1 and 2 show the main parts of the electromagnetic-acoustic measuring apparatus that is the present invention. The reference numbers in the drawings refer to the same parts in every drawing.

Referring to FIGS. 1 and 2, body 1, the body to be inspected, is inserted in the openings of the d.c. coils 11 and 12, which are separate from each other. Coils 11 and 12 are excited by a d.c. source (not shown) so that the magnetic fields (indicated by the broken lines) generated by the coils merge with each other. In this case, the coils 11 and 12 may be connected in series or parallel. The transmitting/receiving coil 13 is placed in the space between the d.c. coils 11 and 12 so as to face body 1. Separate transmitting and receiving coils may also be used, arranged opposite each other on either side of the body 1.

Figure 3:
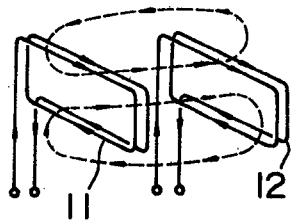
FIG. 3 is a diagram which illustrates the fundamental concepts underlying the embodiment shown in FIG. 1.
Figure 4:
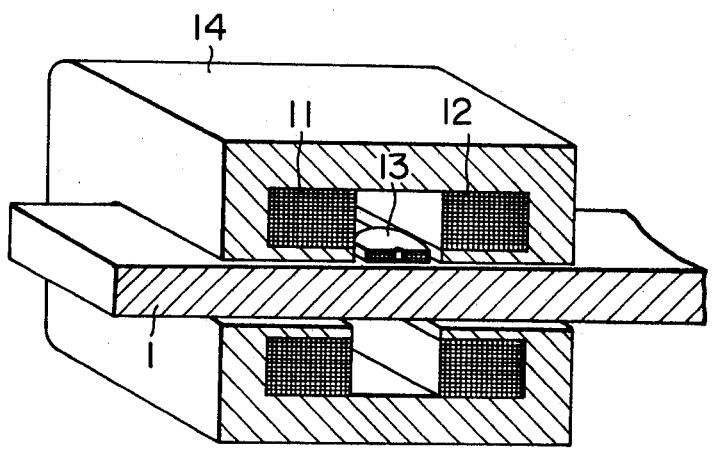
FIG. 4 is a perspective view of another embodiment of the present invention, in cross section, in which an iron core is added to the embodiment shown in FIG. 1.

FIG. 3 shows the exciting currents flowing through the d.c. coils 11 and 12. In FIG. 3, the arrow heads on the solid lines indicate the direction of the d.c. exciting currents. In the above arrangement, the greater parts of the d.c. magnetic flux generated by the d.c. coils 11 and 12 passes through the body 1 parallel to the surface of the body in a longitudinal direction. That is, almost all of the magnetic flux generated by the coils 11 and 12 concentrate in a magnetic field that is parallel to the surface of the body 1. Such a situation is necessary in order to transmit and receive longitudinal electromagnetic-acoustic waves. The intensity of the magnetic field increases as the ampere-turns of the d.c. coils 11 and 12 are increased and, therefore, a field intensity of more than 10,000 gauss can easily be obtained. As a result, the present embodiment is about 11 times as sensitive to longitudinal electromagnetic-acoustic waves as are conventional apparatuses. This is because the strength of transmitter/receiver signals increases according to the relation $(10,000/3,000)^2$, where 3,000 gauss refers to the average field intensity obtainable with conventional apparatuses. In the present invention, the transmitting/receiving coil 13 may be placed on the front, back, or side surface of the body 1 to be inspected so long as it is placed in the magnetic field. It is also possible to place more than one transmitting/receiving coil in the magnetic field. One simple way of increasing the efficiency with which a magnetic field is generated is to add an iron core to the embodiment shown in FIG. 1. FIG. 4 is a perspective view, in cross section, of an embodiment with an iron core. In FIG. 4, the iron core 14 is placed so as to enclose the d.c. coils 11 and 12.

In the case where a superconducting magnet is used in place of an electromagnet with a coil made of a normal conductor, the intensity of the magnetic field in the body 1 can be increased much more and, therefore, sensitivity can also be greatly increased.

Figure 5:
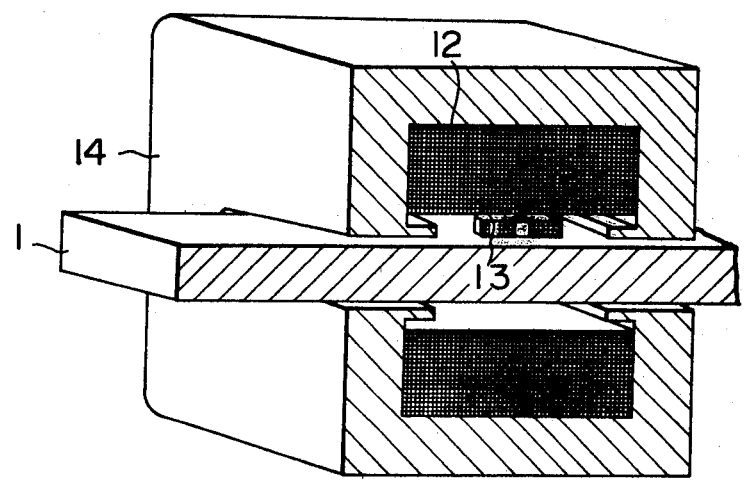
FIG. 5 is a perspective view of yet another embodiment of the present invention, in cross section, in which only a single exciting coil is used.

FIG. 5 shows a different embodiment of an electromagnetic-acoustic measuring apparatus, which includes only one d.c. coil and is, essentially, the same as the embodiment shown in FIG. 4.

Figure 6:
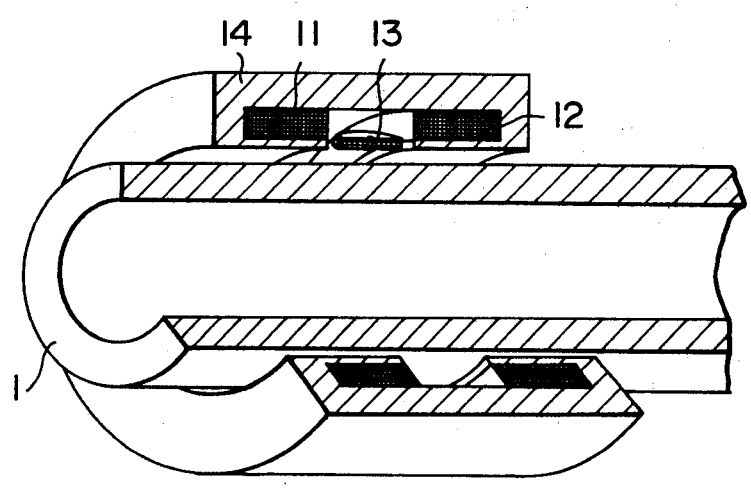
FIG. 6 is a perspective view of yet another embodiment of the present invention, in cross section, in which a pipe is being inspected.

FIG. 6 shows a further embodiment of the present invention, in which the thickness of the wall of pipe 1 is measured. In a practical apparatus, it is better to divide the iron core 14, shown in FIGS. 4 to 6, into two parts, as shown in FIGS. 7 and 8, so that one or two d.c. coils are enclosed and held by those parts.

FIGS. 7 and 8 are side and front views respectively, in partial cross section, of the embodiment shown in FIG. 6. The figures show the structure of the embodiment in detail.

In FIGS. 7 and 8, the iron core 14 is divided into two symmetrical parts 14a and 14b, each of which is U-shaped in cross section and has several holes drilled through its mid-section, to allow other components of the apparatus to be attached. The d.c. coils 11 and 12 are secured to the 14a and 14b inner surfaces of the cores with protective covers 21a and 21b. As shown in FIG. 7, the iron cores 14a and 14b are attached to each other with bolts 22 and nuts (not shown) so that the d.c. coils 11 and 12 face each other. The cylindrical pole pieces 25a and 25b, which have tapered heads, are placed in the holes that were drilled into the iron cores 14a and 14b and then fixed to the cores with bolts 26. The circular plates 27a and 27b, which have holes drilled through their centers, serve as covers. The covers 27a and 27b have several holes drilled through, to allow the bolts 26 are inserted, and has several cut off, to arrange the cooling water pipes are arranged. Since each of the pole pieces 25a and 25b has the tapered head portion, it is possible to concentrate a magnetic field between the head portions. Accordingly, a magnetic field parallel to the surface of the body 1 to be measured can be effectively formed. When the size of the body 1 varies, the pole pieces 25a and 25b are replaced by other appropriate pole pieces. Further, since the inner surface of each of the pole pieces 25a and 25b is inclined as shown in FIG. 7, that is, has the form of a funnel, the body 1 can be smoothly inserted into the pole piece. Further, by bonding a protection member to the inner surface of the pole piece, the body 1 and pole pieces 25a and 25b are prevented from being damaged even if the body 1 strikes against the pole pieces 25a and 25b.

Through-holes are provided in each of the pole pieces 25a and 25b to cause cooling water to flow, thereby cooling the pole pieces. Now, let us consider the side of the iron core 14a, by way of example. Cooling water flows into an inlet pipe 28a, and then flows through a first through-hole in the pole piece 25a. The cooling water having passed through the first through-hole is led at the head portion of the pole piece to a second through-hole, which is provided in the pole piece 25a so as to be spaced 90° apart from the first through-hole, through a connecting pipe (not shown). The cooling water having passed through the second through-hole is led to a third through-hole, which is provided 90° apart from the second through-hole, through a connecting pipe 30a. The cooling water having flowed through the third through-hole is led at the head portion of the pole piece to a fourth through-hole, which is provided 90° apart from the third through-hole, through a connecting pipe 31a. The cooling water having passed through the fourth through-hole is exhausted to the outside through an exit pipe (not shown) which is placed at an upper symmetrical position corresponding to the position of the inlet pipe 28a. That is, the pole piece 25a is provided therein with four parallel through-holes in such a manner that adjacent through-holes are spaced 90° apart from each other, and the cooling water flows through these through-holes to cool the pole piece 25a. Similarly, on the side of the iron core 14b, cooling water flows into an inlet pipe 28b, flows through through-holes in the iron core 25b and connecting pipes (including a connecting pipe 31b), and is then exhausted through an exit pipe (not shown).

As shown in FIG. 7, each of the pole pieces 25a and 25b may be divided along a broken line into inner and outer cylinders, which are then united in one body. In this case, when each pole piece is replaced in accordance with a change in size of the body 1, the inner and outer cylinders can be separately handled. Since each of these cylinders is small in weight as compared with the united pole piece, the replacement of pole piece becomes easy.

A cylindrical block 40 for mounting therein transmitting/receiving parts is made of a flat hollow member and has through-holes 61 to 66 at an interval of 60°. Transmitting/receiving parts 51 to 56 are mounted in the through-holes 61 to 66, respectively. Incidentally, the through-holes 64 and 65 and transmitting/receiving parts 54 and 55 are not shown in FIG. 8. The block 40 is supported by respective head portions of the pole pieces 25a and 25b. The through-holes 61 to 66 provided in the block 40 are provided, on the side of the body 1, with non-conductive covers 71 to 76, respectively, and are provided, on the opposite side, with the transmitting/receiving parts 51 to 56, respectively. Since each transmitting/receiving part is mainly formed of, for example, moulded transmitting and receiving coils (not shown), protection covers 81 to 86 are disposed to reinforce the transmitting/receiving parts 51 to 56.

Electrical connections between an external circuit and every pair of transmitting and receiving coils are made by cables 91 to 96. The cables 91 to 96 are led to the outside through a through-hole provided in the pole piece 25b, in the same manner as an inlet pipe 42 mentioned later. Incidentally, the non-conductive covers 74 and 75, protection covers 84 and 85, and cables 94 and 95 are not shown in FIG. 8.

The inlet pipe 42 is connected to a hollow portion 41 of the block 40 to introduce cooling water into the block 40. The cooling water thus introduced is divided at the hollow portion 41 into two parts, one of which flows into a space between the cover 71 and transmitting/receiving part 51, and the other flows into a space between the cover 72 and transmitting/receiving parts 52. The divided cooling water thus flows through hollow portions and spaces, and is then exhausted to the outside through an exit pipe (not shown) which is provided at a position opposite to that of the inlet pipe 42. The inlet pipe 42 passes through a through-hole 43 provided in the pole piece 25b, and the exit pipe passes through another through-hole.

The inlet pipe 42 and the hollow portion 41 of the block 40 are small in cross section. Accordingly, when an impurity is mixed into the cooling water or an alga is generated therein, the inlet pipe 42 and hollow portion 41 may be clogged or the flow of cooling water in these members 41 and 42 may be put to one side. Thus, there is very fair possibility of insufficient cooling. Therefore, it is preferable to use distilled water as the cooling water and to cause the cooling water to flow at a sufficiently high speed.

We claim:

1. An electromagnetic-acoustic measuring apparatus comprising:
   an exciting coil having an opening hole into which a body to be inspected is to be inserted, said exciting coil being applied with a d.c. voltage to generate a magnetic field in a direction substantially parallel to a surface of said body;
   a transmitting coil for generating mechanical strain in a surface portion of said body, said surface portion being subjected to the action of the magnetic field produced by said exciting coil;
   a receiving coil for detecting said mechanical strain at a surface of said body after said mechanical strain has been propagated in said body;
   a core enclosing surfaces of said exciting coil except a surface facing said body;
   pole pieces supported by said core for supporting at least one of said transmitting and receiving coils; and
   each of inner and outer surfaces of said pole pieces being tapered so as to concentrate said magnetic field at the portion of said body.

2. An electromagnetic-acoustic measuring apparatus according to claim 1, wherein a single coil is used as said transmitting and receiving coils.

3. An electromagnetic-acoustic measuring apparatus according to claim 1, wherein said pole pieces are replacable by other pole pieces utilizing a nut and bolt arrangement adapted to the dimensions of said body.

4. An electromagnetic-acoustic measuring apparatus according to claim 1, wherein at least one of said pole pieces and a least one of said transmitting and receiving coils are provided with cooling pipes for water cooling.

5. An electromagnetic-acoustic measuring apparatus according to claim 1, wherein said pole pieces are shaped to surround the periphery of said body and tapered in a direction toward a portion of the support of said at least one of the transmitting and receiving coils so as to enhance the magnetic field at said portion of the support.

6. An electromagnetic-acoustic measuring apparatus according to claim 1, wherein a plurality of pairs of transmitting and receiving coils are arranged around said body.

7. An electromagnetic-acoustic measuring apparatus according to claim 1, wherein a protection cover made of a nonconductive material is disposed on a side of said transmitting and receiving coils facing said body.

8. An electromagnetic-acoustic measuring apparatus comprising:
   a pair of exciting coils having an opening hole into which a body to be inspected may be inserted, said exciting coils being applied with a small d.c. voltage in such a manner that magnetic fluxes generated by said exciting coils and which are substantially parallel to a surface of the body act on the body in a common direction;
   a pair of cores coupled together by a bolt and nut arrangement for enclosing all surfaces of said exciting coils except a portion facing the body;
   at least one pole piece supported by said cores and facing the body, said pole piece being provided with a tapered end so as to concentrate the magnetic fluxes thereat; and
   coil means including at least one of a transmitting coil for generating mechanical strain in a surface portion of the body proximate to said tapered end of the pole piece when supplied with an a.c. current, the surface portion of the body being subjected to the action of the magnetic fluxes, and a receiving coil for detecting a mechanical strain after the mechanical strain has been propagated in the body, said coil means being supported by said pole piece.

9. An electromagnetic-acoustic measuring apparatus according to claim 8, wherein a plurality of pole pieces are provided, each pole piece being provided with a tapered end.

10. An electromagnetic-acoustic measuring apparatus according to claim 9, wherein said coil means includes a single coil utilized as a transmitting coil and a receiving coil.

11. An electromagnetic-acoustic measuring apparatus according to claim 9, wherein said coil means includes a separate transmitting coil and a separate receiving coil.

12. An electromagnetic-acoustic measuring apparatus according to claim 9, wherein said transmitting coil is disposed on a surface of the body for generating a longitudinal ultrasonic wave in the body.

13. An electromagnetic-acoustic measuring apparatus according to claim 9, further comprising a protection member bonded to an inner surface of said pole pieces for protection of the body.

14. An electromagnetic-acoustic measuring apparatus according to claim 9, wherein said pole pieces are formed of inner and outer cylinders.

15. An electromagnetic-acoustic measuring apparatus according to claim 9, wherein each pole piece tapers in a direction toward a portion of the support for the coil means.

* * * * *